United States Patent [19]

Hopper et al.

[11] 4,086,253
[45] Apr. 25, 1978

[54] 3,3',5,5'-TETRA-SUBSTITUTED DIPHENOQUINONE FROM 2,6-DISUBSTITUTED PHENOL BY PHASE-TRANSFER CATALYSIS

[75] Inventors: Charles R. Hopper; Larry D. Kershner, both of Midland, Mich.

[73] Assignee: The Dow Chemical Company, Midland, Mich.

[21] Appl. No.: 703,481

[22] Filed: Jul. 8, 1976

[51] Int. Cl.$^2$ .................. C07C 45/16; C07C 49/62
[52] U.S. Cl. ................................................ 260/396 N
[58] Field of Search .................................. 260/396 N

[56] References Cited

U.S. PATENT DOCUMENTS

| 2,785,188 | 3/1957 | Coe | 260/396 N |
| 2,905,674 | 9/1959 | Filbey | 260/396 N |

*Primary Examiner*—Vivian Garner
*Attorney, Agent, or Firm*—G. R. Plotecher

[57] ABSTRACT

3,3',5,5'-Tetra-substituted diphenoquinone, such as 3,3',5,5'-tetra-t-butyl-4,4'-diphenoquinone, is efficiently prepared by a process comprising contacting oxygen with a liquid 2,6-disubstituted phenol, such as 2,6-di-t-butylphenol in the presence of aqueous base and a catalytic amount of a phase-transfer catalyst, such as tri-n-butylmethylammonium chloride. This process is characterized by high yields, short reaction times and facile product recovery.

12 Claims, No Drawings

3,3′,5,5′-TETRA-SUBSTITUTED DIPHENOQUINONE FROM 2,6-DISUBSTITUTED PHENOL BY PHASE-TRANSFER CATALYSIS

BACKGROUND OF THE INVENTION

1. Field of the Invention

This invention relates to 3,3′,5,5′-tetra-substituted diphenoquinones. In one aspect, this invention relates to a process of preparing said tetra-substituted diphenoquinones by oxidatively coupling 2,6-disubstituted phenol in an alkaline reaction medium. In another aspect, this invention relates to said process catalyzed by a phase-transfer catalyst.

2. Description of the Prior Art

Filbey, U.S. Pat. No. 2,905,674, teaches preparing 3,3′,5,5′-tetraalkyldiphenoquinones by contacting, in a substantially homogeneous liquid system and under reaction conditions, a 4-halo-2,6-dialkylphenol and a basic compound having an ionization constant characteristic of a base of at least about $1.6 \times 10^{-3}$ at 25° C. The halogen of said phenol has an atomic weight greater than 30 and at least one of the alkyl groups of said phenol is branched. Equimolar amounts of said basic compound and said phenol are used.

Hay, U.S. Pat. Nos. 3,210,384, 3,306,874 and 3,306,875, teaches a process for preparing tetra-substituted diphenoquinones by reacting oxygen with a solution of a 2,6-disubstituted monohydric, monocyclic phenol dissolved in a suitable inert solvent in the presence of a dissolved oxygen-carrying intermediate comprising a basic cupric salt complex of an organic nitrogen-containing compound selected from the group consisting of cyano-substituted hydrocarbons and N,N-di(monovalent hydrocarbon) carbamoyl substituted hydrocarbons. The oxygen-carrying intermediate is also referred to as an amine-basic cupric salt complex.

SUMMARY OF THE INVENTION

According to this invention, 3,3′,5,5′-tetra-substituted diphenoquinone is efficiently prepared by a process comprising contacting oxygen with a liquid 2,6-disubstituted phenol in the presence of aqueous base and a catalytic amount of a phase-transfer catalyst. The tetra-substituted diphenoquinone is recovered in high yields and after short reaction times.

DETAILED DESCRIPTION OF THE INVENTION

The 2,6-disubstituted phenols here used are of the formula

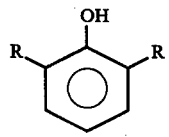

wherein each R is of 1 to about 18 carbon atoms or independently alkyl, alkoxy, aryl and aryloxy. For example, typical alkyls include methyl, ethyl, propyl, isopropyl, butyl, t-butyl, octyl, dodecyl, cyclopropyl, cyclohexyl, and the like; typical alkoxies include methoxy, ethoxy, propoxy, isopropoxy, butoxy, t-butoxy, dodecyloxy, and the like; typical aryls include benzyl, naphthyl, phenethyl, naphthylpropyl, tolyl, phenyl, xylyl and the like; and typical aryloxies include benzyloxy, phenyloxy, and the like. Each R can be either the same or a different monovalent radical. Illustrative 2,6-disubstituted phenols include: 2,6-dimethylphenol, 2,6-diethylphenol, 2-methyl-6-ethylphenol, 2,6-diisopropylphenol, 2,6-di-t-butylphenol, 2,6-dicyclohexylphenol, 2,6-didodecylphenol, 2,6-dimethoxyphenol, 2-methoxy-6-ethoxyphenol, 2-ethyl-6-hexadecyloxyphenol, 2,6-ditolylphenol, 2-phenyl-6-xylylphenol, 2,6-diphenoxyphenol, 2-methyl-6-phenylphenol, 2,6-dibenzyloxyphenol, 2,6-bis-(2′,4′-dichlorophenyl)phenol and the like. The monovalent radicals may bear inert substituents, such as halogen, ester, etc. By inert is meant that the substitutent will not be affected by the invention. Preferably each R is alkyl and of 1 to 8 carbon atoms inclusive, with each R a t-butyl radical most preferred.

The oxygen here used can be either oxygen itself or an oxygen-containing gas, such as air. If desired, the oxygen can be diluted with other gases such as nitrogen or one of the inert gases.

Any suitable base can be used in the practice of this invention. Typically the base is an aqueous alkali metal hydroxide, such as aqueous sodium, potassium, rubidium, and cesium hydroxide, but other strong bases can be used. For example, other strong bases include alkali metal alkoxides, such as sodium and potassium methylate, ethylate and propylate, and nitrogen-containing bases such as guanidine, piperazine, diethylamine, etc. Aqueous alkali metal hydroxides are preferred with aqueous sodium hydroxide especially preferred.

Phase-transfer catalysts are here used and any such catalyst that will catalyze the basic, oxidative coupling of 2,6-disubstituted phenol is suitable. Due to their general familiarity, onium salts are the preferred phase-transfer catalysts with the quaternary ammonium and phosphonium salts especially preferred. These salts are described by Starks and Napier in Br 1,227,144 and by Starks in J. Amer. Chem. Soc., 93, 195 (1971). Suitable onium salts have a minimum solubility of at least about 1 weight percent in both the organic phase and the aqueous phase at 25° C. Tri-n-butylmethyl-, triphenylmethyl-, benzyltriethyl-, and tetra-n-butylammonium and phosphonium chlorides, bromides and bisulfates are the most preferred phase-transfer catalysts.

As a further illustration of the type of onium salts here used, suitable ammonium salts are represented by the formula $R'R''R'''R^{IV}N^{\oplus}A^{\ominus}$ wherein N is a quaternized nitrogen atom, $R'$—$R^{IV}$ are hydrocarbyl groups, i.e., alkyl, aryl, alkylaryl, cycloalkyl, etc., and R′ can join with R″, or R″ with R‴, etc. to form a 5- or 6-membered heterocyclic compound having at least one quaternized nitrogen atom in the ring and may also contain one nonadjacent atom of nitrogen, oxygen or sulfur within the ring. Typically, $R'$—$R^{IV}$ are hydrocarbyl groups of from 1 to about 16 carbon atoms each with a combined minimum total of about 10 carbon atoms. Preferred ammonium salts have from about 10 to about 30 carbon atoms. A similar formula can be drawn for the phosphonium salts.

The neutralizing anion portion of the salt, i.e., $A^{\ominus}$ in the above formula, may be varied to convenience. Chloride and bromide are the preferred anions but other representative anions include fluoride, iodide, tosylate, acetate, bisulfate, etc. The following compounds serve as a nonlimiting illustration: tetraalkylammonium salts, such as tetra-n-butyl-, tri-n-butylmethyl-, tetrahexyl-, trioctylmethyl-, hexadecyltriethyl-, and tridecylmethylammonium chlorides, bromides, iodides, bisulfates, tosylates, etc.; aralkylammonium salts, such as tetrabenzyl-, benzyltrimethyl-, benzyltriethyl-, benzyltributyl-, and phenethyltrimethylammonium chlorides, bromides, iodides, etc.; arylammonium salts, such as triphenylmethylammonium fluoride, chloride or bromide, N,N,N-trimethyl-N-phenylammonium chloride, N,N,N-triethyl-N-phenylammonium bromide, N,N-diethyl-N,N-diphenylammonium bisulfate, trimethylnaphthylammonium chloride, p-methylphenyltrimethyl ammonium chloride or tosylate, etc.; 5- and 6- membered heterocyclic compounds containing at least one quaternary nitrogen atom in the ring, such as N,N-dibutylmorpholinium chloride, N-decylthiazolium chloride, etc., and the corresponding phosphonium salts.

At least stoichiometric amounts of oxygen and 2,6-disubstituted phenol are used. An excess of oxygen will insure a quantitative conversion of the 2,6-disubstituted phenol to the corresponding quinone whereas an excess of a 2,6-disubstituted phenol will only insure quantitative consumption of oxygen.

Excess base is generally employed in the practice of this invention although any suitable amount (based on the 2,6-disubstituted phenol) can be used. A base: disubstituted phenol mole ratio of about 5:1 is a typical maximum, with a said mole ratio of about 2.5:1 as a preferred maximum. There is no minimum amount of base required for this invention other than sufficient base to render the reaction mixture alkaline. However, since base amount directly influences reaction rate, practical considerations of reaction time, convenience, etc. prefer a base: disubstituted phenol mole ratio of about 0.5:1 as a typical minimum.

A catalytic amount of the phase-transfer catalyst is required in the practice of this invention. The concentration will vary with the particular reagents employed but the best results are generally achieved when the maximum phase-transfer catalyst concentration is about 30 mole percent, and preferably about 10 mole percent, with a minimum phase-transfer catalyst concentration of about 1 mole percent and preferably of about 2 mole percent (based on the 2,6-disubstituted phenol).

Of course, since the 2,6-disubstituted phenol is an organic compound (and used in liquid form) and aqueous base is used, the reaction medium is a biphasic, liquid mixture. Although the reaction can be conducted neat, it is preferably conducted in the presence of an inert, water-immiscible organic solvent which not only aids in the formation of a biphasic mixture, but also aids in moderating the reaction rate and temperature. Typical solvents include: benzene, chlorobenzene, o-dichlorobenzene, hexane, methylene chloride, chloroform, carbon tetrachloride, and the like.

In a preferred mode of practice, the solvent of choice is o-dichlorobenzene. Not only are both 2,6-disubstituted phenol and the corresponding reaction product soluble in this solvent, thus allowing the product to be easily washed and separated from the aqueous base, but it also has a high boiling point and thus reduces solvent loss. Moreover, because of its high boiling point, the invention can be practiced at higher temperatures. This allows the reaction to proceed at a faster rate (without a loss in yield) than rates taught in the prior art.

Typically, like 2,6-disubstituted phenol molecules are coupled to form a quinone, such as two molecules of 2,6-di-t-butylphenol to form 3,3',5,5'-tetra-t-butyl-4,4'-diphenoquinone. However, unlike 2,6-disubstituted phenol molecules can also be coupled to form a quinone, such as 2,6-diethylphenol and 2,6-dipropylphenol to form 3,5-diethyl-3',5'-dipropyl-4,4'-diphenoquinone.

This invention can be practiced at any temperature and pressure at which the biphasic mixture remains a liquid. Best results are obtained when the reaction temperature is between about 30° and about 100° C, inclusive, at atmospheric pressure.

The following examples are illustrative embodiments of this invention.

SPECIFIC EMBODIMENTS

EXAMPLE 1

2,6-Di-t-butylphenol (10 g, 0.05 mole), o-dichlorobenzene (50 g, 0.34 mole), water (15 g, 0.83 mole), sodium hydroxide (4.85 g, 0.12 mole) and tri-n-butylmethylammonium chloride (0.5 g, 0.002 mole) were added to a 250 ml round bottom flask fitted with a stirring device and then heated to and maintained at 50° C. The flask contents were then subjected to aspirator vacuum and subsequently blanketed with oxygen. The oxygen was supplied in such a manner that as the oxygen was consumed, additional oxygen was introduced, thus maintaining a constant pressure. The contents were vigorously stirred and the reaction monitored by measuring oxygen consumption. At the cessation of oxygen consumption, analysis of the flask contents revealed 3,3',5,5'-tetra-t-butyl-diphenoquinone in excess of 90 percent yield.

If desired, the reaction product can be recovered from the flask contents by washing the contents with water and decanting same and then crystallizing the 3,3',5,5'-tetra-t-butyl-diphenoquinone from the organic solvent.

EXAMPLE 2

Example 1 was repeated except triphenylmethylphosphonium bromide (0.5 g, 0.001 mole) was substituted for tri-n-butylmethylammonium chloride. About a 90 percent yield of 3,3',5,5'-tetra-t-butyl-diphenoquinone was obtained.

What is claimed is:

1. A process of preparing 3,3',5,5'-tetra-substituted diphenoquinone comprising contacting oxygen with a liquid 2,6-disubstituted phenol of the formula

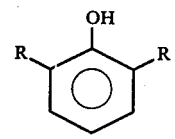

wherein each R is of 1 to about 18 carbon atoms and independently alkyl, alkoxy, aryl or aryloxy in the presence of aqueous strong base and a catalytic amount of an onium salt of the formula $R'R''R'''R^{IV}Q^{\oplus}A^{\ominus}$ wherein $Q^{\oplus}$ is a quaternized nitrogen or phosphorus atom, $A^{\ominus}$ is a neutralizing anion, and $R'—R^{IV}$ are hydrocarbyl groups of 1 to about 16 carbon atoms each with a combined minimum total of about 10 carbon atoms, or any two members of $R'—R^{IV}$ are joined to form a 5- or 6-membered heterocyclic compound, said compound having at least one quaternized nitrogen or phosphorus atom in the ring and said compound having an optional nonadjacent atom of nitrogen, oxygen or sulfur within the ring.

2. The process of claim 1 wherein the 2,6-disubstituted phenol is dissolved in an inert, water-immiscible organic solvent.

3. The process of claim 2 wherein the base and 2,6-disubstituted phenol are present at a base: 2,6-disubstituted phenol mole ratio between about 0.5:1 and about 5:1, inclusive.

4. The process of claim 3 wherein the onium salt is present in an amount between about 1 and about 30 mole percent, inclusive, based on the 2,6-disubstituted phenol.

5. The process of claim 4 wherein the base is selected from the group consisting of alkali metal hydroxides, alkali metal alkoxides, and nitrogen-containing bases.

6. The process of claim 5 wherein the base is an alkali metal hydroxide.

7. The process of claim 3 wherein the onium salt is present in an amount between about 2 and about 10 mole percent, inclusive, based on the 2,6-disubstituted phenol.

8. The process of claim 7 wherein the onium salt is tri-n-butylmethyl-, benzyltriethyl-, triphenylmethyl- or tetra-n-butylammonium or phosphonium chloride, bromide, or bisulfate.

9. The process of claim 8 wherein the base is sodium hydroxide.

10. The process of claim 9 wherein the 2,6-disubstituted phenol is 2,6-di-t-butylphenol.

11. The process of claim 10 wherein the inert, water-immiscible organic solvent is benzene, chlorobenzene or o-dichlorobenzene.

12. The process of claim 11 wherein the contacting is conducted at a temperature between about 30° and about 100° C, inclusive, and at atmospheric pressure.

* * * * *